United States Patent [19]

Brake

[11] Patent Number: 4,870,008

[45] Date of Patent: Sep. 26, 1989

[54] SECRETORY EXPRESSION IN EUKARYOTES

[75] Inventor: Anthony J. Brake, Berkeley, Calif.

[73] Assignee: Chiron Corporation, Emeryville, Calif.

[21] Appl. No.: 81,302

[22] Filed: Aug. 3, 1987

Related U.S. Application Data

[63] Continuation of Ser. No. 522,909, Aug. 12, 1983, abandoned, which is a continuation-in-part of Ser. No. 457,325, Jan. 12, 1983, abandoned.

[51] Int. Cl.[4] .................... C12P 21/02; C12N 15/00; C12N 1/12; C12N 1/00
[52] U.S. Cl. .................................. 435/70; 435/172.3; 435/256; 435/320; 935/37; 935/48
[58] Field of Search ...................... 435/172.3, 320, 70, 435/256; 935/48, 37

[56] References Cited

U.S. PATENT DOCUMENTS

| | | | |
|---|---|---|---|
| 4,338,397 | 6/1982 | Gilbert et al. | 435/68 |
| 4,546,082 | 10/1985 | Kurjan et al. | 435/317 |

FOREIGN PATENT DOCUMENTS

| | | |
|---|---|---|
| 46039 | 2/1982 | European Pat. Off. |
| 60057 | 9/1982 | European Pat. Off. |
| 73635 | 3/1983 | European Pat. Off. |
| 88632 | 9/1983 | European Pat. Off. |
| 123294 | 10/1984 | European Pat. Off. |
| 123544 | 10/1984 | European Pat. Off. |
| 128733 | 12/1984 | European Pat. Off. |
| WO83/04030 | 11/1983 | PCT Int'l Appl. |
| WO84/01173 | 3/1984 | PCT Int'l Appl. |
| 2100737 | 1/1983 | United Kingdom |
| 2104902 | 3/1983 | United Kingdom |
| 2162851 | 2/1986 | United Kingdom |

OTHER PUBLICATIONS

Kurjan et al., The Molecular Biology of Yeast (abstract book), p. 242 (11–16 Aug. 1981).
Blair et al., The Molecular Biology of Yeast (abstract book), p. 243, (Aug. 1981).
Kurjan et al. (1982), Cell 30:933–943.
Smith et al. (1982), Nucleic Acids Res., 10:4467–4482.
Hitzeman et al. (1983), Science, 219:620–624.
Brake et al. (1984), Proc. Natl. Acad. Sci., USA, 81:4642–4644.
Hishinuma et al., in *Molecular Biology of Yeast: Abstracts of Papers Presented at the 1985 Meeting*, p. 309 (Cold Spring Harbor Laboratory, 1985).
Julius et al. (1983), Cell, 32:839–852.
Brake et al. (1983), Molec. & Cell. Biol., 3:1440–1450.
Fuller et al. in *Microbiology* 1986, pp. 273–278 (1986).

*Primary Examiner*—Alvin E. Tanenholtz
*Attorney, Agent, or Firm*—Robert P. Blackburn

[57] ABSTRACT

Methods and compositions are provided for producing polypeptide sequences in high yield by employing DNA constructs, wherein the DNA sequence encoding from the polypeptide of interest in preceded by a leader sequence and processing sequence for secreting and processing said polypeptide. In this manner, the mature polypeptide of interest may be isolated from the nutrient medium substantially free of major amounts of other proteins and cellular debris.

The yeast strain *S. cerevisiae* AB103 (pYEGF8) was deposited on Jan. 5, 1983, at the A.T.C.C. and given accession No. 20658.

The plasmid pYαEGF23 (pAB114-pCl/1) was deposited at the A.T.C.C. on Aug. 12, 1983, and given Accession No. 40079.

37 Claims, 2 Drawing Sheets

```
                                                                                          80
                                                                                     Gly Val Ser Leu Asp Lys Arg Glu Ala Glu    Asn Ser Asp Ser Glu
                                                                                          85        90            /       5
                                                                                a. GGG GTA TCT TTG GAT AAA AGA GAG GCT GAA GCT GAA AAC TCC GAC TCC GAA      (pYαEGF-21)
                                                                                   CCC CAT AGA AAC CTA TTT TCT CTC CGA CTT CGA CTT TTG AGG CTG AGG CTT
                                                                                                                         Linker-1

80                                              /        5
                                                                                     Gly Val Ser Leu Asp Lys Arg Glu Ala Glu Ala Ser Leu Asp Lys Arg Asn Ser Asp Ser Glu
                                                                                          85        90
                                                                                b. GGG GTA TCT TTG GAT AAA AGA GAG GCT GAA GCT TCT TTG GAT AAA AGA AAC TCC GAC TCC GAA     (pYαEGF-22)
                                                                                   CCC CAT AGA AAC CTA TTT TCT CTC CGA CTT CGA AGA AAC CTA TTT TCT TTG AGG CTG AGG CTT
                                                                                                                                     Linker-2

80                                        /        5
                                                                                     Gly Val Ser Leu Asp Lys Arg    Asn Ser Asp Ser Glu
                                                                                          85
                                                                                c. GGG GTA TCT TTG GAT AAA AGA AAC TCC GAC TCC GAA         (pYαEGF-23)
                                                                                   CCC CAT AGA AAC CTA TTT TCT TTG AGG CTG AGG CTT

80                                        /        5
                                                                                     Gly Val Pro Leu Asp Lys Arg    Asn Ser Asp Ser Glu
                                                                                          85
                                                                                d. GGG GTA CCT TTG GAT AAA AGA AAC TCC GAC TCC GAA         (pYαEGF-24)
                                                                                   CCC CAT GGA AAC CTA TTT TCT TTG AGG CTG AGG CTT

80                                                /        5
                                                                                     Gly Val Gln Leu Asp Lys Arg    Asn Ser Asp Ser Glu
                                                                                        PvuII        Linker-3
                                                                                e. GGG GTA CAG CTG GAT AAA AGA AAC TCC GAC TCC GAA         (pYαEGF-25)
                                                                                   CCC CAT GTC GAC CTA TTT TCT TTG AGG CTG AGG CTT
                                                                                        CAT GTC GAC
                                                                                     50          53
                                                                                   Trp Trp Glu Leu Arg            Linker-4
                                                                                f. TGG TGG GAA TTG AGA TGA TAA GTC GAC CGA TG
                                                                                   ACC ACC CTT AAC TCT ACT ATT CAG CTG GCT AC

FIG. 2.
```

SECRETORY EXPRESSION IN EUKARYOTES

This application is a continuation of Ser. No. 522,909, filed 12 Aug. 1983, and now abandoned which is a continuation-in-part of Ser. No. 457,325, filed 12 Jan. 1983 and now abandoned.

BACKGROUND OF THE INVENTION

1. Field of the Invention

Hybrid DNA technology has revolutionized the ability to produce polypeptides of an infinite variety of compositions. Since living forms are composed of proteins and employ proteins for regulation, the ability to duplicate these proteins at will offers unique opportunities for investigating the manner in which these proteins function and the use of such proteins, fragments of such proteins, or analogs in therapy and diagnosis.

There have been numerous advances in improving the rate and amount of protein produced by a cell. Most of these advances have been associated with higher copy numbers, more efficient promoters, and means for reducing the amount of degradation of the desired product. It is evident that it would be extremely desirable to be able to secrete polypeptides of interest, where such polypeptides are the product of interest.

Furthermore, in many situations, the polypeptide of interest does not have an initial methionine amino acid. This is usually a result of there being a processing signal in the gene encoding for the polypeptide of interest, which the gene source recognizes and cleaves with an appropriate peptidase. Since in most situations, genes of interest are heterologous to the host in which the gene is to be expressed, such processing occurs imprecisely and in low yield in the expression host. In this case, while the protein which is obtained will be identical to the peptide of interest for almost all of its sequence, it will differ at the N-terminus which can deleteriously affect physiological activity.

There are, therefore, many reasons why it would be extremely advantageous to prepare DNA sequences, which would encode for the secretion and maturing of the polypeptide product Furthermore, where sequences can be found for processing, which result in the removal of amino acids superfluous to the polypeptide of interest, the opportunity exists for having a plurality of DNA sequences, either the same or different, in tandem, which may be encoded on a single transcript.

2. Description of the Prior Art

U.S. Pat. No. 4,336,336 describes for prokaryotes the use of a leader sequence coding for a noncytoplasmic protein normally transported to or beyond the cell surface, resulting in transfer of the fused protein to the periplasmic space. U.S. Pat. No. 4,338,397 describes for prokaryotes using a leader sequence which provides for secretion with cleavage of the leader sequence from the polypeptide sequence of interest. U.S. Pat. No. 4,338,397, columns 3 and 4, provide for useful definitions, which definitions are incorporated herein by reference.

Kurjan and Herskowitz, Cell (1982) 30:933-943 describes a putative α-factor precursor containing four tandem copies of mature α-factor, describing the sequence and postulating a processing mechanism. Kurjan and Herskowitz, Abstracts of Papers presented at the 1981 Cold Spring Harbor meeting on The Molecular Biology of Yeasts, page 242, in an Abstract entitled, "A Putative α-Factor Precursor Containing Four Tandem Repeats of Mature α-Factor," describe the sequence encoding for the α-factor and spacers between two of such sequences. Blair et al., Abstracts of Papers, ibid, page 243, in an Abstract entitled "Synthesis and Processing of Yeast Pheremones: Identification and Characterization of Mutants That Produce Altered α-Factors," describe the effect of various mutants on the production of mature o-factor.

SUMMARY OF THE INVENTION

Methods and compositions are provided for producing mature polypeptides. DNA constructs are provided which join the DNA fragments encoding for a yeast leader sequence and processing signal to heterologous genes for secretion and maturation of the polypeptide product. The construct of the DNA encoding for the N-terminal cleavable oligopeptide and the DNA sequence encoding for the mature polypeptide product can be joined to appropriate vectors for introduction into yeast or other cell which recognizes the processing signals for production of the desired polypeptide. Other capabilities may also be introduced into the construct for various purposes

BRIEF DESCRIPTION OF THE DRAWINGS

FIG. 2 shows sequences at fusions of hEGF to the vector. a. through e. show the sequences at the N-terminal region of hEGF, which differ among several constructions and f. shows the C-terminal region of hEGF.

DESCRIPTION OF THE SPECIFIC EMBODIMENTS

Figure 1:
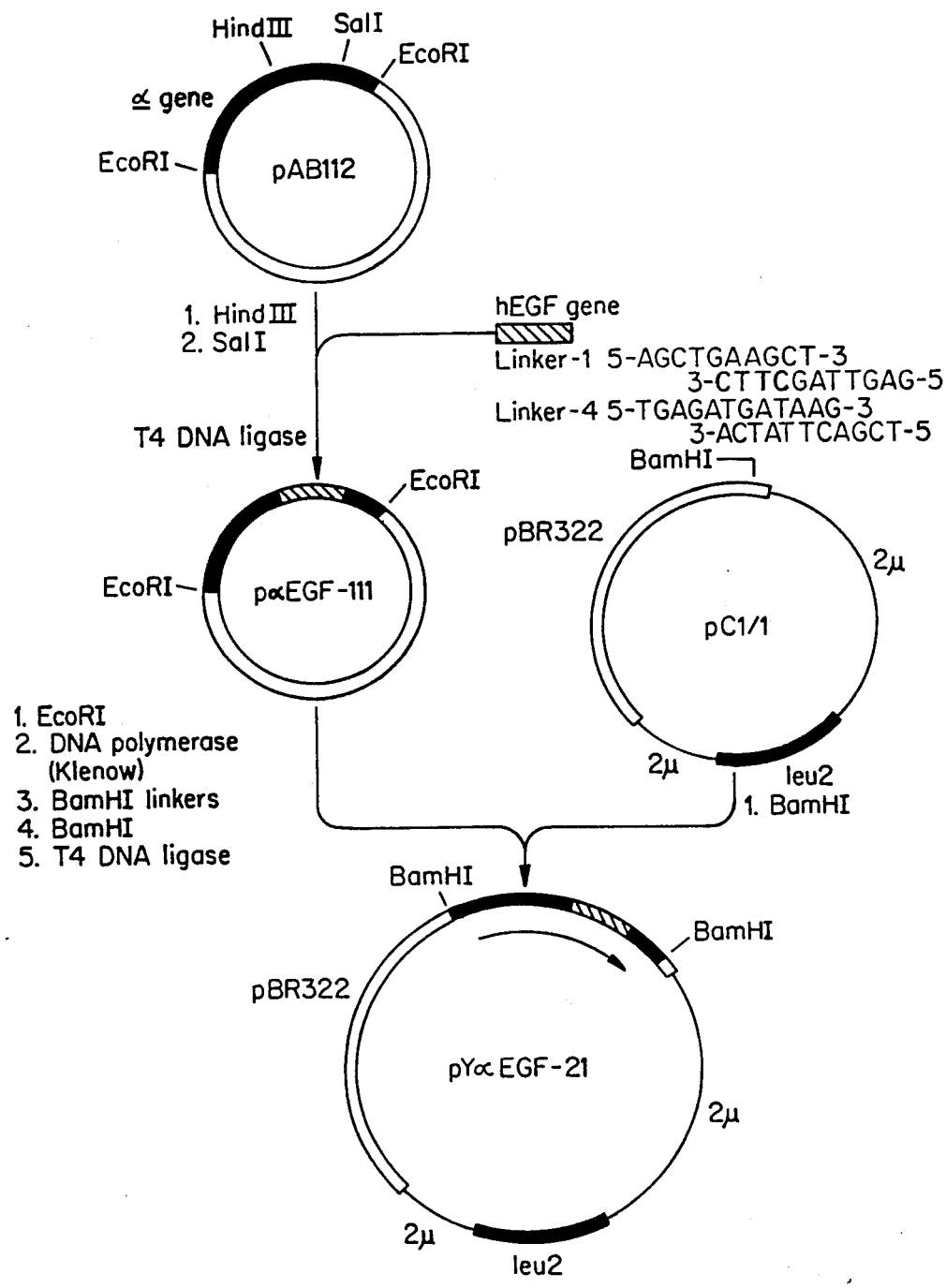
FIG. 1 is a flow diagram indicating the construction of pYαEGF-21.

In accordance with the subject invention, eukaryotic hosts, particularly yeast are employed for the production of mature polypeptides, where such polypeptides may be harvested from a nutrient medium. The polypeptides are produced by employing a DNA construct encoding for yeast leader and processing signals joined to a polypeptide of interest, which may be a single polypeptide or a plurality of polypeptides separated by processing signals. The resulting construct encodes for a pre-pro-polypeptide which will contain the signals for secretion of the pre-pro-polypeptide and processing of the polypeptide, either intracellularly or extracellularly to the mature polypeptide.

The constructs of the subject invention will have at least the following formula defining a pro-polypeptide:

$$((R)_r-(GAXYCX)_n-Gene^*)_y$$

wherein:

R is CGX or AZZ, the codons coding for lysine and arginine, each of the Rs being the same or different;

r is an integer of from 2 to 4, usually 2 to 3, preferably 2 or 4;

X is any of the four nucleotides, T, G, C, or A;

Y is G or C;

y is an integer of at least one and usually not more than 10, more usually not more than four, providing for monomers and multimers;

Z is A or G; and

Gene* is a gene other than α-factor, usually foreign to a yeast host, usually a heterologous gene, desirably a plant or mammalian gene;

n is 0 or an integer which will generally vary from 1 to 4, usually 2 to 3.

The pro-polypeptide has an N-terminal processing signal for peptidase removal of the amino acids preceding the amino acids encoded for by Gene*.

For the most part, the constructs of the subject invention will have at least the following formula:

L—(R—S—(GAXYCX)$_n$)-Gene*)$_y$ defining a pre-pro-polypeptide, wherein all the symbols except L and S have been defined, S having the same definition as R, there being 1R and 1S, and L is a leader sequence providing for secretion of the pre-pro-polypeptide. While it is feasible to have more Rs and Ss there will usually be no advantage in the additional amino acids. Any leader sequence may be employed which provides for secretion, leader sequences generally being of about 30 to 120 amino acids, usually about 30 to 100 amino acids, having a hydrophobic region and having a methionine at its N-terminus.

The construct when n is 0 will have the following formula:

L—((R)$_{r'}$—Gene*)$_y$ defining a pre-pro-polypeptide,
wherein all the symbols have been defined
previously, except r', wherein:
r' is 2 to 4, preferably 2 or 4.

Of particular interest is the leader sequence of α-factor which is described in Kurjan and Herskowitz, supra, on page 937 or fragments or analogs thereof, which provide for efficient secretion of the desired polypeptides. Furthermore, the DNA sequence indicated in the article, which sequence is incorporated herein by reference, is not essential, any sequence which encodes for the desired oligopeptide being sufficient. Different sequences will be more or less efficiently translated.

While the above formulas are preferred, it should be understood, that with suppressor mutants, — other sequences could be provided which would result in the desired function. Normally, suppressor mutants are not as efficient for expression and, therefore, the above indicated sequence or equivalent sequence encoding for the same amino acid sequence is preferred. To the extent that a mutant will express from a different codon the same amino acids which are expressed by the above sequence, then such alternative sequence could be permitted.

The dipeptides which are encoded for by the sequence in the parenthesis will be an acidic amino acid, aspartic or glutamic, preferably glutamic, followed by a neutral amino acid, alanine and proline, particularly alanine.

In providing for useful DNA sequences which can be used for cassettes for expression, the following sequence can be conveniently employed:

Tr—L—((R—S)$_{r'}$—(GAXYCX)$_{n'}$—W—(Gene*)$_d$)$_y$ wherein:
Tr intends a DNA sequence encoding for the transcriptional regulatory signals, particularly the promoter and such other regulatory signals as operators, activators, cap signal, signals enhancing ribosomal binding, or other sequence involved with transcriptional or translational control. The Tr sequence will generally be at least about 100 bp and not more than about 2000 bp. Particularly useful is employing the Tr sequence associated with the leader sequence L, so that a DNA fragment can be employed which includes the transcriptional and translational signal sequences associated with the leader sequence endogenous to the host. Alternatively, one may employ other transcriptional and translational signals to provide for enhanced production of the expression product;

d is 0 or 1, being 1 when y is greater than 1;

n' is a whole number, generally ranging 0 to 3, more usually being 0 or 2 to 3;

r" is 1 or 2;

W intends a terminal deoxyribosyl-3' group, or a DNA sequence which by itself or, when n' is other than 0, in combination with the nucleotides to which it is joined, W defines a restriction site, having either a cohesive end or butt end, wherein W may have from 0 to about 20 nucleotides in the longest chain;

the remaining symbols having been defined previously.

Of particular interest is the following construct:

(Tr)$_a$—L—(R—S)$_{r''}$—(GAXYCX)$_{n''}$GA⌈AGGT⌉ wherein:
all of the symbols previously defined have the same definition;

a is 0 or 1 intending that the construct may or may not have the transcriptional and translational signals; the nucleotides indicated in the broken are intended not to be present but to be capable of addition by adding an HindIII cleaved terminus to provide for the recreation of the sequence encoding for a dipeptide; and n" will be 0 to 2, where at least one of the Xs and Ys defines a nucleotide, so that the sequence in the parenthesis is other than the sequence GAAGCT.

The coding sequence of Gene* may be joined to the terminal T, providing that the coding sequence is in frame with the initiation codon and upon processing the first amino acid will be the correct amino acid for the mature polypeptide.

The 3'-terminus of Gene* can be manipulated much more easily and, therefore, it is desirable to provide a construct which allows for insertion of Gene* into a unique restriction site in the construct. Such a construct would provide for a restriction site with insertion of the Gene* into the restriction site to be in frame with the initiation codon. Such a construction can be symbolized as follows:

(Tr)a—L—(R—S)$_{r''}$—(GAXYCX)$_{n''}$—W—(SC)$_b$—Te wherein
those symbols previously defined have the same definition;

SC are stop codons;

Te is a termination sequence balanced with the promoter Tr, and may include other signals, e.g. polyadenylation; and b is an integer which will generally vary from about 0 to 4, more usually from 0 to 3, it being understood, that Gene* may include its own stop codons.

Illustrative of a sequence having the above formula is where W is the sequence GA and n" is 2.

Of particular interest is where the sequence encoding the terminal dipeptide is taken together with W to define a linker or connector, which allows for recreation of the terminal sequence defining the dipeptide of the processing signal and encodes for the initial amino acids of Gene*, so that the codons are in frame with the initiation codon of the leader. The linker provides for a staggered or butt ended termination, desirably defining a restriction site in conjunction with the successive sequences of the Gene*. Upon ligation of the linker with Gene*, the codons of Gene* will be in frame with the initiation codon of the leader. In this manner, one can employ a synthetic sequence which may be joined to a restriction site in the processing signal sequence to recreate the processing signal, while providing the initial bases of the Gene* encoding for the N-terminal amino acids By employing a synthetic sequence, the synthetic linker can be a tailored connector having a convenient restriction site near the 3'-terminus and the synthetic connector will then provide for the necessary codons for the 5'-terminus of the gene.

Alternatively, one could introduce a restriction endonuclease recognition site downstream from the processing signal to allow for cleavage and removal of superfluous bases to provide for ligation of the Gene* to the processing signal in frame with the initiation codon. Thus the first codon would encode for the N-terminal amino acid of the polypeptide Where T is the first base of Gene*, one could introduce a restriction site where the recognition sequence is downstream from the cleavage site. For example, a Sau3A recognition sequence could be introduced immediately after the processing signal, which would allow for cleavage and linking of the Gene* with its initial codon in frame with the leader initiation codon. With restriction endonucleases which have the recognition sequence distal and downstream from the cleavage site e.g. HgaI, W could define such sequence which could include a portion of the processing signal sequences. Other constructions can also be employed, employing such techniques as primer repair and in vitro mutagenesis to provide for the convenient insertion of Gene* into the construct by introducing an appropriate restriction site.

The construct provides a portable sequence for insertion into vectors, which provide the desired replication system. As already indicated, in some instances, it may be desirable to replace the wild type promoter associated with the leader sequence with a different promoter In yeast, promoters involved with enzymes in the glycolytic pathway can provide for high rates of transcription. These promoters are associated with such enzymes as phosphoglucoisomerase, phosphofructokinase, phosphotriose isomerase, phosphoglucomutase, enolase, pyruvic kinase, glyceraldehyde-3-phosphate dehydrogenase, and alcohol dehydrogenase. These promoters may be inserted upstream from the leader sequence The 5'-flanking region to the leader sequence may be retained or replaced with the 3'-sequence of the alternative promoter. Vectors can be prepared and have been reported which include promoters having convenient restriction sites downstream from the promoter for insertion of such constructs as described above.

The final construct will be an episomal element capable of stable maintenance in a host, particularly a fungal host such as yeast. The construct will include one or more replication systems, desirably two replication systems, allowing for maintenance in the expression host and cloning in a prokaryote. In addition, one or more markers for selection will be included, which will allow for selective pressure for maintenance of the episomal element in the host. Furthermore, the episomal element may be a high or low copy number, the copy number generally ranging from about 1 to 200. With high copy number episomal elements, there will generally be at least 10, preferably at least 20, and usually not exceeding about 150, more usually not exceeding about 100 copy number. Depending upon the Gene*, either high or low copy numbers may be desirable, depending upon the effect of the episomal element on the host. Where the presence of the expression product of the episomal element may have a deleterious effect on the viability of the host, a low copy number may be indicated.

Various hosts may be employed, particularly mutants having desired properties. It should be appreciated that depending upon the rate of production of the expression product of the construct, the processing enzyme may or may not be adequate for processing at that level of production. Therefore, a mutant having enhanced production of the processing enzyme may be indicated or enhanced production of the enzyme may be provided by means of an episomal element. Generally, the production of the enzyme should be of a lower order than the production of the desired expression product.

Where one is using α-factor for secretion and processing, it would be appropriate to provide for enhanced production of the processing enzyme Dipeptidyl Amino Peptidase A, which appears to be the expression product of STE13. This enzyme appears to be specific for X-Ala- and X-Pro-sequences, where X in this instance intends an amino acid, particularly, the dicarboxylic acid amino acids.

Alternatively, there may be situations where intracellular processing is not desired. In this situation, it would be useful to have a ste13 mutant, where secretion occurs, but the product is not processed. In this manner, the product may be subsequently processed in vitro.

Host mutants which provide for controlled regulation of expression may be employed to advantage. For example, with the constructions of the subject invention where a fused protein is expressed, the transformants have slow growth which appears to be a result of toxicity of the fused protein. Thus, by inhibiting expression during growth, the host may be grown to high density before changing the conditions to permissive conditions for expression.

A temperature-sensitive sir mutant may be employed to achieve regulated expression. Mutation in any of the SIR genes results in a non-mating phenotype due to in situ expression of the normally silent MATa and MATα sequences present at the HML and HMR loci.

Furthermore, as already indicated, the Gene* may have a plurality of sequences in tandem, either the same or different sequences, with intervening processing signals. In this manner, the product may be processed in whole or in part, with the result that one will obtain the various sequences either by themselves or in tandem for subsequent processing. In many situations, it may be desirable to provide for different sequences, where each of the sequences is a subunit of a particular protein product.

The Gene* may encode for any type of polypeptide of interest. The polypeptide may be as small as an oligopeptide of 8 amino acids or may be 100,000 daltons or higher. Usually, single chains will be less than about 300,000 daltons, more usually less than about 150,000 daltons. Of particular interest are polypeptides of from about 5,000 to 150,000 daltons, more particularly of about 5,000 to 100,000 daltons. Illustrative polypeptides of interest include hormones and factors, such as growth hormone, somatomedins epidermal growth factor, the endocrine secretions, such as luteinizing hormone, thyroid stimulating hormone, oxytocin, insulin, vasopressin, renin, calcitonin, follicle stimulating hormone, prolactin, etc.; hematopoietic factors, e.g. erythropoietin, colony stimulating factor, etc.; lymphokines; globins; globulins, e.g. immunoglobulins; albumins; interferons, such as α, β and γ; repressors; enzymes; endorphins e.g. β-endorphin, enkephalin, dynorphin, etc.

Having prepared the episomal elements containing the constructs of this invention, one may then introduce such element into an appropriate host. The manner of introduction is conventional, there being a wide variety of ways to introduce DNA into a host. Conveniently, spheroplasts are prepared employing the procedure of, for example, Hinnen et al., PNAS U.S.A. (1978) 75:1919–1933 or Stinchcomb et al., EP No. 0 045 573 A2. The transformants may then be grown in an appropriate nutrient medium and where appropriate, maintaining selective pressure on the transformants. Where expression is inducible, one can allow for growth of the yeast to high density and then induce expression. In those situations, where a substantial proportion of the product may be retained in the periplasmic space, one can release the product by treating the yeast cells with an enzyme such as zymolase or lyticase.

The product may be harvested by any convenient means, purifying the protein by chromatography, electrophoresis, dialysis, solvent-solvent extraction, etc.

In accordance with the subject invention, one can provide for secretion of a wide variety of polypeptides, so as to greatly enhance product yield, simplify purification, minimize degradation of the desired product, and simplify processing, equipment, and engineering requirements. Furthermore, utilization of nutrients based on productivity can be greatly enhanced, so that more economical and more efficient production of polypeptides may be achieved. Also, the use of yeast has many advantages in avoiding enterotoxins, which may be present with prokaryotes, and employing known techniques, which have been developed for yeast over long periods of time, which techniques include isolation of yeast products.

The following examples are offered by way of illustration and not by way of limitation.

EXPERIMENTAL

A synthetic sequence for human epidermal growth factor (EGF) based on the amino acid sequence of EGF reported by H. Gregory and B.M. Preston Int. J. Peptide Protein Res. 9, 107–118 (1977) was prepared, which had the following sequence.

fragment. The HgaI-HindIII linker had the following sequence:

```
AGCTGAAGCT
    CTTCGATTGAG
```

This linker restores the α-factor processing signals interrupted by the HindIII digestion and joins the HgaI end at the 5'-end of the EGF gene to the HindIII end of pAB112.

The HgaI-SalI linker had the following sequence:

```
TGAGATGATAAG
    ACTATTCAGCT
```

This linker has two stop codons and joins the HgaI end at the 3'-end of the EGF gene to the SalI end of pAB112.

The resulting 181 base pair fragment was purified by preparative gel electrophoresis and ligated to 100ng of pAB112 which had been previously completely digested with the enzymes HindIII and SalI. Surprisingly, a deletion occurred where the codon for the 3rd and 4th amino acids of EGF, asp and ser, were deleted, with the remainder of the EGF being retained.

pAB112 is a plasmid containing a 1.75kb EcoRI fragment with the yeast α-factor gene cloned in the EcoRI site of pBR322 in which the HindIII and SalI sites had been deleted pAB112 was derived from plasmid pAB101 which contains the yeast α-factor gene as a partial Sau3A fragment cloned in the BamHI site of plasmid YEp24. pAB101 was obtained by screening a yeast genomic library in YEp24 using a synthetic 20-mer oligonucleotide probe (3'-GGCCGGTTGGTTACATGATT-5') homologous to the published α-factor coding region (Kurjan and Herskowitz, Abstracts 1981 Cold Spring Harbor meeting on the Molecular Biology of Yeasts, page 242).

The resulting mixture was used to transform E. coli HB101 cells and plasmid pAB201 obtained. Plasmid pAB201 (5μg) was digested to completion with the enzyme EcoRI and the resulting fragments were: a) filled in with DNA polymerase I Klenow fragment; b) ligated to an excess of BamHI linkers; and c) digested with BamHI. The 1.75kbp EcoRI fragment was isolated by preparative gel electrophoresis and approximately 100ng of the fragment was ligated to 100ng of pC1/1,

```
5' AACTCCGACTCCGAATGTCCATTGTCCCACGACGGTTACTGTTTGCACGACGGTGTTTGT
3' TTGAGGCTGAGGCTTACAGGTAACAGGGTGCTGCCAATGACAAACGTGCTGCCACAAACA
   ATGTACATCGAAGCTTTGGACAAGTACGCTTGTAACTGTGTTGTTGGTTACATCGGTGAA
   TACATGTAGCTTCGAAACCTGTTCATGCGAACATTGACACAACAACCAATGTAGCCACTT
   AGATGTCAATACAGAGACTTGAAGTGGTGGGAATTGAGATGA
   TCTACAGTTATGTCTCTGAACTTCACCACCCTTAACTCTACT,
``` where 5' indicates the promoter proximal end of the sequence. The sequence was inserted into the EcoRI site of pBR328 to produce a plasmid p328EGF-1 and cloned.

Approximately p328EGF-1 was digested with EcoRI and approximately 1μg of the expected 190 base pair EcoRI fragment was isolated. This was followed by digestion with the restriction enzyme HgaI. Two synthetic oligonucleotide connectors HindIII-HgaI and HgaI-SalI were then ligated to the 159 base pair HgaI which had been previously digested to completion with the restriction enzyme BamHI and treated with alkaline phosphatase.

Plasmid pC1/1 is a derivative of pJDB219, Beggs, Nature (1978) 275:104, in which the region corresponding to bacterial plasmid pMB9 in pJDB219 has been replaced by pBR322 in pC1/1. This mixture was used to transform E. coli HB101 cells. Transformants were selected by ampicillin resistance and their plasmids analyzed by restriction endonucleases. DNA from one selected clone (pYEGF-8) was prepared and used to transform yeast AB103 cells. Transformants were selected by their leuphenotype.

Fifty milliliter cultures of yeast strain AB103 (α, pep 4-3, leu 2-3, leu 2-112, ura 3-52, his 4-580) transformed with plasmid pYEGF-8 were grown at 30° in -leu medium to saturation (optical density at 600nm of 5) and left shaking at 30° for an additional 12 hr period. Cell supernatants were collected by centrifugation and analyzed for the presence of human EGF using the fibroblast receptor competition binding assay. The assay of EGF is based on the ability of both mouse and human EGF to compete with $^{125}$I-labeled mouse EGF for binding sites on human foreskin fibroblasts. Standard curves can be obtained by measuring the effects of increasing quantities of EGF on the binding of a standard amount of $^{125}$I-labeled mouse EGF. Under these conditions 2 to 20 ng of EGF are readily measureable. Details on the binding of 125I-labeled epidermal growth factor to human fibroblasts have been described by Carpenter et al., J. Biol. Chem. 250, 4297 (1975). Using this assay it is found that the culture medium contains 7±1mg of human EGF per liter.

For further characterization, human EGF present in the supernatant was purified by absorption to the ion-exchange resin Biorex-70 and elution with HCl 10mM in 80% ethanol. After evaporation of the HCl and ethanol the EGF was solubilized in water. This material migrates as a single major protein of MW approx. 6,000 in 17.5% SDS gels, roughly the same as authentic mouse EGF (MW-6,000). This indicates that the α-factor leader sequence has been properly excised during the secretion process. Analysis by high resolution liquid chromatography (microbondapak C18, Waters column) indicates that the product migrates with a retention time similar to an authentic mouse EGF standard. However, protein sequencing by Edman degradation showed that the N-terminus retained the glu-ala sequence.

A number of other constructions were prepared using different constructions for joining hEGF to the α-factor secretory leader sequence, providing for different processing signals and site mutagenesis. In FIG. 2 a. through e. show the sequence of the fusions at the N-terminal region of hEGF, which sequence differ among several constructions. f. shows the sequences at the C-terminal region of hEGF, which is the same for all constructions. Synthetic oligonucleotide linkers used in these constructions are boxed.

These fusions were made as follows. Construction (a) was made as described above. Construction (b) was made in a similar way except that linker 2 was used instead of linker 1. Linker 2 modifies the α-factor processing signal by inserting an additional processing site (ser-leu-asp-lys-arg) immediately preceding the hEGF gene. The resulting yeast plasmid is named pYαEGF-22. Construction (c), in which the dipeptidyl aminopeptidase maturation site (glu-ala) has been removed, was obtained by in vitro mutagenesis of construction (a). A PstI-SalI fragment containing the α-factor leader-hEGF fusion was cloned in phage M13 and isolated in a single-stranded form. A synthetic 31-mer of sequence 5'-TCTTTGGATAAAAGAAACTCCGACTCCCG-3' was synthesized and 70 picomoles were used as a primer for the synthesis of the second strand from 1 picomole of the above template by the Klenow fragment of DNA polymerase. After fill-in and ligation at 14° for 18 hrs, the mixture was treated with S$_1$ nuclease (5 units for 15 min) and used to transfect *E. coli* JM101 cells. Bacteriophage containing DNA sequences in which the region coding for (glu-ala) was removed were located by filter plaque hybridization using the $^{32}$P-labeled primer as probe. RF DNA from positive plaques was isolated, digested with PstI and SalI and the resulting fragment inserted in pAB114 which had been previously digested to completion with SalI and partially with PstI and treated with alkaline phosphatase.

The plasmid pAB114 was derived as follows: plasmid pAB112 was digested to completion with HindIII and then religated at low (4μg/ml) DNA concentration and plasmid pAB113 was obtained in which three 63bp HindIII fragments have been deleted from the α-factor structural gene, leaving only a single copy of mature α-factor coding region. A BamHI site was added to plasmid pAB11 by cleavage with EcoRI, filling in of the overhanging ends by the Klenow fragment of DNA polymerase, ligation of BamHI linkers, cleavage with BamHI and religation to obtain pAB12. Plasmid pAB113 was digested with EcoRI, the overhanging ends filled in, and ligated to BamHI linkers. After digestion with BamHI the 1500bp fragment was gel-purified and ligated to pAB12 which had been digested with BamHI and treated with alkaline phosphatase. Plasmid pAB114, which contains a 1500bp BamHI fragment carrying the α-factor gene, was obtained. The resulting plasmid (pAB114 containing the above described construct) is then digested with BamHI and ligated into plasmid pC1/1.

The resulting yeast plasmid is named pYαEGF-23. Construction (d), in which a new KpnI site was generated, was made as described for construction (c) except that the 36-mer oligonucleotide primer of sequence 5'-GGGTACCTTTGGATAAAAGAAACTC-CGACTCCGAAT-3' was used. The resulting yeast plasmid is named pYαEGF-24. Construction (e) was derived by digestion of the plasmid containing construction (d) with KpnI and SalI instead of linker 1 and 2. The resulting yeast plasmid is named pYαEGF-25.

Yeast cells transformed with pYαEGF-22 were grown in 15 ml cultures. At the indicated densities or times, cultures were centrifuged and the supernatants saved and kept on ice. The cell pellets were washed in lysis buffer (0.1 Triton X-100, 10mM NaHPO$_4$ pH 7.5) and broken by vortexing (5min in 1min intervals with cooling on ice in between) in one volume of lysis buffer and one volume of glass beads. After centrifugation, the supernatants were collected and kept on ice. The amount of hEGF in the culture medium and cell extracts was measured using the fibroblast receptor binding competition assay. Standard curves were obtained by measuring the effects of increasing quantities of mouse EGF on the binding of a standard amount 125I-labeled mouse EGF.

Proteins were concentrated from the cul media by absorption on Bio-Rex 70 resin and elution with 0.01 HCl in 80% ethanol and purified by high performance liquid chromatography (HPLC) on a reverse phase C18 column. The column was eluted at a flow rate of 4ml/min with a linear gradient of 5% to 80% acetonitrile containing 0.2% trifluoroacetic acid in 60 min. Proteins (200-800 picomoles) were sequenced at the amino-terminal end by the Edman degradation method using a gas-phase protein sequencer Applied Biosystems model 470A. The normal PROTFA program was used for all the analyses. Dithiothreitol was added to S2 (ethyl acetate: 20mg/liter) and S3 (butyl chloride: 10mg/liter) immediately before use. All samples were treated with 1N HCl in methanol at 40° for 15min to convert PTHaspartic acid and PTH-glutamic acid to their methyl esters. All PTH-amino acid identifications were performed by reference to retention times on a IBM CN HPLC column using a known mixture of PTH-amino acids as standards.

Secretion from pYαEGF-22 gave a 4:1 mole ratio of native N-terminus hEGF to glu-ala terminated hEGF, while secretion from pYαEGF-23-25 gave only native N-terminated hEGF. Yields of hEGF ranged from 5 to 8λg/ml measured either as protein or in a receptor binding assay.

The strain JRY188 (MAT sir3-8 leu2-3 leu2-112 trpl ura3 his4 rme) was transformed with pYαEGF-21 and lucine prototrophs selected at 37°. Saturated cultures were then diluted 1/100 in fresh medium and grown in leucine selective medium at permissive (24°) and non-permissive (36°) temperatures and culture supernatants were assayed for the presence of hEGF as described above. The results are shown in the following table.

| Regulated synthesis and secretion of hEGF in transformed yeast sir3 temperature-sensitive mutants. | | | |
|---|---|---|---|
| Temperature | Transformant | O.D. 650 | hEGF(μg/ml) |
| 36° | 3a | 3.5 | 0.010 |
|  |  | 5.4 | 0.026 |
|  | 3b | 3.6 | 0.020 |
|  |  | 6.4 | 0.024 |
| 24° | 3a | 0.4 | 34 |
|  |  | 1.3 | 145 |
|  |  | 2.1 | 1075 |
|  |  | 4.0 | 3250 |
|  | 3b | 0.4 | 32 |
|  |  | 1.4 | 210 |
|  |  | 2.2 | 1935 |
|  |  | 4.2 | 4600 |

These results indicate that the hybrid α-factor/EGF gene is being expressed under mating type regulation, even though it is present on a high copy number plasmid.

In accordance with the subject invention, novel constructs are provided which may be inserted into vectors to provide for expression of polypeptides having an N-terminal leader sequence and one or more processing signals to provide for secretion of the polypeptide as well as processing to result in a mature polypeptide product free of superfluous amino acids. Thus, one can obtain a polypeptide having the identical sequence to a naturally occurring polypeptide. In addition, because the polypeptide can be produced in yeast, glycosylation can occur, so that products can be obtained which are identical to the naturally occurring products. Furthermore, because the product is secreted, greatly enhanced yields can be obtained based on cell population and processing and purification are greatly simplified. In addition, employing mutant hosts, expression can be regulated to be turned off or on, as desired.

Although the foregoing invention has been described in some detail by way of illustration and example for purposes of clarity of understanding, it will be obvious that certain changes and modifications may be practiced within the scope of the appended claims.

What is claimed is:

1. A DNA construct comprising a sequence of the following formula:

$$5'—L—S—Gene\ *—3,$$

where:
L encodes a Saccharomyces alpha-factor leader sequence recognized by a yeast host for secretion;
S encodes a spacer sequence providing processing signals resulting in the enzymatic processing by said yeast host of a precursor polypeptide encoded y L—S—Gene * into the polypeptide encoded by Gene *, S containing the sequence $5'—R_1—R_2—3'$ immediately adjacent to the sequence Gene *, $R_1$ being a codon for lysine or arginine, $R_2$ being a codon for arginine, with the proviso that S not contain the sequence $5'—R_3—R_4—X—3'$, where $R_3=R_1$, $R_4=R_2$, and X encodes a processing signal for dipeptidylaminopeptidase A; and
Gene * encodes a polypeptide foreign to Saccharomyces.

2. The DNA construct of claim 1 having the formula:

$$5'—Tr—L—S—Gene\ *-Te-3,$$

where
Tr is a sequence defining transcriptional and translational regulatory signals for initiation and processing of transcription and translation in said yeast host, and
Te is a transcription termination sequence balanced with said Tr.

3. The DNA construct of claim 2 wherein S is $5'—R_1—R_2—3'$.

4. The DNA construct of claim 3 wherein $R_1$ is a codon for lysine.

5. The DNA construct of claim 2 wherein Tr comprises an alpha-factor promoter sequence.

6. The DNA construct of claim 4 wherein Tr comprises an alpha-factor promoter sequence.

7. The DNA construct of claim 2 wherein Gene * encodes a mammalian protein.

8. The DNA construct of claim 4 wherein Gene * encodes a mammalian protein.

9. The DNA construct of claim 5 wherein Gene * encodes a mammalian protein.

10. The DNA construct of claim 7 wherein said mammalian protein is human epidermal growth factor.

11. The DNA construct of claim 8 wherein said mammalian gene is human epidermal growth factor.

12. The DNA construct of claim 9 wherein said mammalian protein is human epidermal growth factor.

13. The DNA construct of claim 2 wherein said alpha-factor is S. cerevisae alpha-factor.

14. The DNA construct of claim 6 wherein said alpha-factor is S. cerevisae alpha-factor.

15. The DNA construct of claim 11 wherein said alpha-factor is S. cerevisae alpha-factor.

16. An episomal expression element comprising a DNA construct according to claim 2 and a replication system providing stable maintenance in said yeast host.

17. An episomal expression element comprising a DNA construct according to claim 4 and a replication system providing stable maintenance in said yeast host.

18. An episomal expression element comprising a DNA construct according to claim 5 and a replication system providing stable maintenance in said yeast host.

19. An episomal expression element comprising a DNA construct according to claim 7 and a replication system providing stable maintenance in said yeast host.

20. An episomal expression element comprising a DNA construct according to claim 10 and a replication system providing stable maintenance in said yeast host.

21. An episomal expression element comprising a DNA construct according to claim 11 and a replication system providing stable maintenance in said yeast host.

22. In a method of producing a polypeptide foreign to a yeast host, said method comprising providing a yeast host transformed by a DNA construct encoding a hybrid protein comprising said polypeptide fused at the N-terminal to an amino acid sequence comprising a Saccharomyces alpha-factor leader sequence recognized by said yeast host for secretion, wherein said leader sequence is from a Saccharomyces alpha-factor precursor polypeptide containing a dipeptidylaminopeptidase A processing signal for the processing of said precursor, and growing said transformed yeast host in culture under conditions whereby said polypeptide is secreted into the culture medium, the improvement comprising employing A DNA construct the does not encode a dipeptidylaminopeptidase A processing signal in said N-terminal amino acid sequence so that dipepetidylaminopeptidase A process of said hybrid protein is eliminated.

23. The method of claim 22 wherein said DNA construct is contained on an episomal expression element.

24. The method of claim 22 wherein said yeast host is of the genus Saccharomyces.

25. The method of claim 24 wherein said yeast host is *S. Cerevisiae*.

26. The method of claim 22 wherein said polypeptide is a mammalian polypeptide.

27. The method of claim 26 wherein said mammalian polypeptide is human epidermal growth factor.

28. The method of claim 23 wherein said episomal expression element is pyαEGF23.

29. Plasmid pYαEGF23.

30. Plasmid pYEGF8.

31. *S cerevisiae* AB103 transformed by plasmid pYeGF8.

32. A method of producing a polypeptide foreign to yeast and having said polypeptide secreted into the culture medium, said method comprising:
   growing in said culture medium yeast transformed by a DNA construct according to claim 2 under conditions whereby the polypepitde defined by the sequence L—S—Gene * is expressed, processed, and secreted into said culture medium; and
   recovering from said culture medium a polypeptide defined by the sequence Gene * free of superfluous amino acids at the N-terminus.

33. A method of producing a polypeptide foreign to yeast and having said polypeptide secreted in the culture medium, said method comprising:
   growing in said culture medium yeast transformed by an episomal expression element according to claim 6 under conditions whereby the polypeptide defined by the sequence L—S—Gene * is expressed, processed, and secreted into said culture mediums; and
   recovering from said culture medium a polypeptide defined by the sequence Gene * free of superfluous amino acids at the N-terminus.

34. The method of claim 32 wherein said yeast is of the genus Saccharomyces.

35. The method of claim 33 wherein said yeast is of the genus Saccharomyces.

36. The method of claim 33 wherein said yeast is a mutant that permits external regulation of expression.

37. The method of claim 33 wherein said yeast is a temperature-sensitive sir mutant.

* * * * *